United States Patent
Uecker et al.

(10) Patent No.: US 6,240,394 B1
(45) Date of Patent: *May 29, 2001

(54) METHOD AND APPARATUS FOR AUTOMATICALLY GENERATING ADVISORY INFORMATION FOR PHARMACY PATIENTS

(75) Inventors: Robert Anthony Uecker, Chesterfield; Michael James Ward, St. Genevieve, both of MO (US); Baxter Hayes Byerly, Jr., Clermont, FL (US)

(73) Assignee: Catalina Marketing International, Inc., St. Petersburg, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/764,139

(22) Filed: Dec. 12, 1996

(51) Int. Cl.$^7$ ............................................. G06F 17/60
(52) U.S. Cl. ............................................. 705/3; 705/14
(58) Field of Search ............................. 705/2, 3, 4, 14

(56) References Cited

U.S. PATENT DOCUMENTS

| | | | |
|---|---|---|---|
| 4,554,446 | 11/1985 | Murphy et al. | 235/487 |
| 4,672,377 | 6/1987 | Murphy et al. | 340/825.34 |
| 4,673,802 | 6/1987 | Ohmae et al. | 705/17 |
| 4,674,041 | 6/1987 | Lemon et al. | 705/14 |
| 4,723,212 | 2/1988 | Mindrum et al. | 705/14 |
| 4,847,764 | 7/1989 | Halvorson | 364/479.01 |
| 4,908,761 | 3/1990 | Tai | 705/14 |
| 4,910,672 | 3/1990 | Off et al. | 705/14 |
| 5,056,019 | 10/1991 | Schultz et al. | 705/14 |
| 5,256,863 | 10/1993 | Ferguson et al. | 80/24 |
| 5,299,121 | 3/1994 | Brill et al. | 705/2 |
| 5,305,196 | 4/1994 | Deaton et al. | 705/10 |
| 5,353,218 | 10/1994 | DeLapa et al. | 705/14 |
| 5,515,270 | 5/1996 | Weinblatt | 705/14 |
| 5,597,995 | 1/1997 | Williams et al. | 235/375 |
| 5,621,812 | 4/1997 | Deaton et al. | 705/14 |
| 5,644,723 | 7/1997 | Deaton et al. | 705/14 |
| 5,649,114 | 7/1997 | Deaton et al. | 705/14 |
| 5,659,469 | 8/1997 | Deaton et al. | 705/14 |
| 5,737,396 | 4/1998 | Garcia | 364/400 |
| 5,758,095 | 5/1998 | Albaum et al. | 705/2 |
| 5,774,868 | 6/1998 | Cragun et al. | 705/14 |
| 5,832,457 | 11/1998 | O'Brien et al. | 705/14 |

OTHER PUBLICATIONS

Henry Gilgoff, "It's Your Money/Prescription: Get It In Writing", Newsday, Aug. 11, 1996, 3 pages.

(List continued on next page.)

Primary Examiner—Eric W. Stamber
(74) Attorney, Agent, or Firm—Jeffrey N. Giunta; John J. Halak

(57) ABSTRACT

A system for generating targeted advisory messages for pharmacy patients based on selected monitored data components of each transaction. When a pharmacy computer prints transaction data, the system monitors the data using printer data capture hardware interposed between the pharmacy computer and its printer. An additional processor compares selected components of the monitored transaction data with preselected combinations of the these components in a database. The database associates the preselected combinations of transaction data components with advisory message components retrieved from the database and used to build an advisory message for output to a printer, which may be the pharmacy computer or an additional printer. Targeting of the advisory messages is based on selected combinations of the identity of the drug being dispensed to the patient, the patient's age and gender, the new or renewal status of the prescription, and the identity of the party primarily responsible for payment to the pharmacy for the transaction.

16 Claims, 7 Drawing Sheets

OTHER PUBLICATIONS

"Envoy links with pharmacies", The Tennessean, Jul. 27, 1996, 1 page.

"ProxyMed Expands Its Electronic Scripts Reach", Health Data Network News, Nov. 6, 1995, 2 pages.

"The Pharmacy Fund Announces Strategic Alliance With Software Vendors To Provide Seamless Access To Rapid Rxemit; High–Tech Rapid Rxemit Financial Service Improves Cash Flow For Pharmacists", Business Wire, Jul. 15, 1996, 3 pages.

Michael F. Conlan, "In–Your–Face Pharmacy", Drug Topics, Jul. 8, 1996, 8 pages.

Annmarie Sarsfield, "Seniors touch screens to access medical facts The Agency for Health Care Administration will place free–standing, easy to use computers in Pinellas for a 3–month trial period", The Tampa Tribune, May 21, 1996, 2 pages.

Michael Wilke, "Actmedia Tries Coupons in Pharmacies", Advertising Age, May 6, 1996, 1 page.

"Software Supplement Your Pharmacy Practice", Computer Talk, vol. 16 No. 3, May/Jun. 1996, 10 pages.

"Pharmacies bolster marketing", Chain Drug Review, May 6, 1996, 2 pages.

"Medi–Span Enters Coupon Business With Target Rx", By Medi–Span, May 1996, 1 page.

"Neuman Distributors, Inc. Launches Interactive Kiosks Offering Consumers Information And High Value Instant Coupons", PR Newswire, Apr. 15, 1996, 2 pages.

Robin Foote—President, "Medi–Link$^{SM}$ Coupon System Rolls–out at Wakefern, Snyder, May's, and Pharmhouse", Medi–Link, Apr. 11, 1996, 13 pages.

Doran Froke, "AdAge Daily Fax" ActMedia, Apr. 9, 1996, 2 pages.

"Healthpoint Introduces Clinical Information To Increase Practice Productivity And Enhance Care; Healthpoint Acs Unveiled At Himss Annual Convention", Business Wire, Mar. 5, 1996, 3 pages.

"Coupon Vehicles Set for Pharmacies", Information Technology, Jan. 15, 1996, 1 page.

Pat Natschke Lenius, "Coupon vehicles set for pharmacies. (Newsletters to be given to consumers of certain pharmaceuticals)", Supermarket News, Jan. 15, 1996, 2 pages.

CounseLabels, Liberty Bell Pharmacy, Jan. 11, 1996, 1 page.

"Medi–Link Offers Point–Of–CareCoupon Promotions", Creative, Dec. 1, 1995, 1 page.

Greg Muirhead, "Computer support", Nov. 6, 1995, 1 page.

Christina Veiders "Retailers expanding health information/coupon systems. (Health Resource and Medi–Link)", Supermarket News, Oct. 9, 1995, 2 pages.

Michael Slezak, "Programming pharmacy's future", American Druggist, Oct. 1, 1995, 8 pages.

"Drug Emporium adopts Rx system", Chain Drug Review, Sep. 25, 1995, vol. 17, No. 18, 1 page.

"The Pharmacy Field Remains Split Over An Electronic Prescription Standard", Automated Medical Paymenst News, Aug. 20, 1995, 2 pages.

"National Data Corporation Announces Affiliation With National Network Of Preferred Vendors", PR Newswire, Jun. 5, 1996, 2 pages.

"Grocers Check Out High Tech To Survive", Advertising Age, May 8, 1995, 1 page.

"Drug Emporium Tries Out Medi–Link Coupon System", RX Marketplace, May 1, 1995, 1 page.

David Vaczek, "Kroger, Wakefern Testing Pharmacy Coupon Systems", Pharmacy Retailing, Apr. 1995, 1 page.

"Prescription Pharmaceuticals and Biotechnology", F–D–C Reports, Apr. 24, 1995, vol. 57, No. 17, 1 page.

"Health product manufacturers using interactive P–O–P. (Point–of–purchase marketing)", Potentials in Marketing, Mar. 1, 1995, 2 pages.

Allen Symons, "Do–it–yourself shopping at its best. (Home Select kiosk)", Drug Store News, Feb. 6, 1995, 2 pages.

Jennifer Reingold, "Cardinal rule. (Drug wholesaler Cardinal Health; includes related article)", Financial World, Jan. 31, 1995, 5 pages.

Tina Cassidy, "Confusion reigns over checking and credit card law", P&L Publication Inc. Boston Business Journal, Apr. 6, 1992, pp. 7–10.

Bob Mannarino, "The Schedule of the presentations at the May 1991 FMI Chicago Conference and the Mannarino publication", May 6, 1991, 21 pages.

"Point of Scan, Electronic Frequent Shopper Programs", Jan. 1991, 3 pages.

Mollie Neal, "Quaker's direct hit; Quaker Oats Co.'s advertising subsidiary Quaker Direct", Hoke Communications Inc. Direct Marketing, Jan. 1991, pp. 3–6.

Sue Lawmaster, "Checkout Savings System and Frequency Marketing Overview", Catalina publication, Dec. 10, 1990, 34 pages.

Tom Wilson, "Market Imaging Systems, Inc./ Catalina Marketing Corporation", Sep. 18, 1990, 21 pages.

"Frequency Programs: Cashing in on Promotions", The Marketing Institute, Sep 11 & 12, 1990, pp. 1–38.

Cathy Cebulski, "P&G, Central Trust develop electronic marketing system", The Greater Cincinnati Business Group, Mar. 26–Apr. 1, 1990, 1 page.

Michael McDermott, "Supermarkets become marketing–driven for the 1990's", Adweeks Marketing Week v31, n12, p50, 2 pages.

"Bar Codes Capture Info", Target Marketing, v12, n1, p52, 1 page.

Martha Groves, "Frequent–Shopper Plans Are Wooing Consumers", Los Angeles Times, Oct. 1, 1989, 4 pages.

MIchael Gates, "The Unfulfilled Promise", Incentive, Database Marketing, Sep. 1989, pp. 123–130.

"Scanning a New Horizon; Food Marketing Research Through Computerized Frequent Buyer Programs", Aug. 1989, pp. 16–18.

"Bar Codes Capture Info", Target Marketing, Jan. 1989, v12, n1, p52, 1 page.

Richard Schulman, "Electronic Marketing: a big stakes game for the retailer and manufacturer", Supermarket Business, v43, n2, p21, 3 pages.

Disclosure by Applicants, by Baxter H. Byerly, dated Jul. 15, 1999 and consisting of 5 pages.

METHOD AND APPARATUS FOR AUTOMATICALLY GENERATING ADVISORY INFORMATION FOR PHARMACY PATIENTS

BACKGROUND OF THE INVENTION

This invention relates generally to point-of-sale systems for use in pharmacies and, more specifically, to systems for automatically generating advisory and other information for distribution to pharmacy patients. Various systems have been used to distribute advisory and other information to pharmacy patients based principally on the identification of a prescription drug being purchased. Prescription drugs in the United States are uniquely identifiable by a National Drug Code (NDC), which is typically entered into a computer terminal by a pharmacist, and may be encoded on the product itself in bar-code form. Other prescription drug identification systems are employed in other countries, but the principle is the same: to provide a unique code for each prescription drug dispensed by the pharmacy. Based on the nature of the drug, a computer at the point of sale may be used to generate advisory messages to the patient, some of which may be required by governmental regulation, or to generate promotional materials concerning related or complementary products sold in the pharmacy.

Although such systems available prior to the present invention are satisfactory for some purposes, the advisory messages they provide are not always appropriately focused on the probable needs of the patients purchasing the drugs. Moreover, systems existing and proposed prior to the present invention typically require major software or hardware changes to existing pharmacy computer systems, the principal function of which is to print prescription labels, simple advisory messages and billing information. Ideally, additional functions should be provided without the need for major modification of existing pharmacy computer systems, other than to generate any additional data needed for the new functions. The present invention meets this objective, as further explained in the summary below.

SUMMARY OF THE INVENTION

The present invention resides in a method and apparatus for generating advisory and other information without major modification of an existing pharmacy computer system. Briefly, and in general terms, the method of the invention comprises the steps of capturing a data record pertaining to a pharmacy transaction as transmitted to a pharmacy printer; comparing selected components of the captured data record with corresponding components of a database to determine the contents of a message associated with particular values of the data components; building an output message based on the results of the comparing step; and transmitting the output message to a printer in the pharmacy, to print an advisory message that is appropriate for the particular values of the data components defining the transaction. The selected data components include any combination of the identity of the dispensed product, the patient's age and gender, the identity of a party primarily responsible for payment to the pharmacy for the transaction and an indication of whether the transaction is based on a new or a refill prescription. Based on these factors, the advisory message can be tailored to the particular transction. Moreover, this goal is achieved without major modification of the existing pharmacy computer system.

In the context of the present invention, the terms "message" and "advisory message" include all types of information provided to pharmacy patients, including information about the prescribed product being dispensed, information about related products or procedures, promotional materials or discounts pertaining to the purchase of prescription products or other products, or simply news items pertaining to the dispensed product or to pharmaceutical products and health in general. The information may take the form of multiple-color, two-sided papers, depending on the available printer technology. Some of the information may be generated as a result of a patient condition inferred from, other factors, such as the patient's age and the type of medication prescribed.

The invention may also be defined in terms of apparatus for generating targeted messages to pharmacy patients, for use in a pharmacy computer system having a pharmacy processor and at least one printer. The apparatus comprises a hardware interface interposed between the pharmacy processor and the printer or printers, to monitor pharmacy data pertaining to each transaction in which a pharmacy product is dispensed to a patient; a database containing advisory message data in association with preselected combinations of components of transaction data; an additional processor, for comparing transaction data components monitored in each transaction with the preselected combinations of transaction data components in the database, wherein the advisory message data components associated with the monitored transaction data components are retrieved from the database; and wherein the additional processor also includes means for building an advisory message from the retrieved advisory message data components; and means for printing the advisory message for distribution to the patient whose transaction is being monitored. As in the method, the preselected combinations of transaction data components include the identity of the dispensed product, the patient's age and gender, the identity of the party primarily responsible for payment to the pharmacy for the transaction, and an indication of whether the transaction is a new or a refill prescription.

The hardware interface in the apparatus may take any of various forms, depending primarily on the configuration of the existing pharmacy computer system. For example, if the pharmacy computer outputs data in parallel format to its printer, the hardware interface includes a parallel-to-serial data converter, for sending monitored data in serial form to the additional processor, and the means for printing the advisory message includes a parallel data connection from the additional processor to the hardware interface and means within the hardware interface for mediating printer conflicts arising between print data transmitted from the pharmacy processor and print data transmitted from the additional processor. If the pharmacy computer outputs data in serial format to a printer, the hardware interface includes a serial data tap, for monitoring the serial data for transmission to the additional processor, and the means for printing the advisory message includes a parallel data connection from the additional processor to the printer, which has both parallel and serial ports and which includes means for mediating printer conflicts arising between print data received through the parallel and serial ports.

It will be appreciated from the foregoing that the present invention represents a significant advance in providing information to pharmacy patients. In particular, more targeted information can be provided in an automatic and convenient manner, without having to make significant modifications to existing pharmacy computer systems. Another important advantage of the invention is that, because it "eavesdrops" passively to obtain data from the pharmacy system print stream, any malfunction in the invention apparatus does not affect basic operation of the pharmacy system, which can continue to process prescriptions and print labels. Other aspects and advantages of the invention will become apparent from the more detailed description; that follows, taken in conjunction with the drawings, which are briefly described below.

DESCRIPTION OF THE PREFERRED EMBODIMENTS

Figure 1:
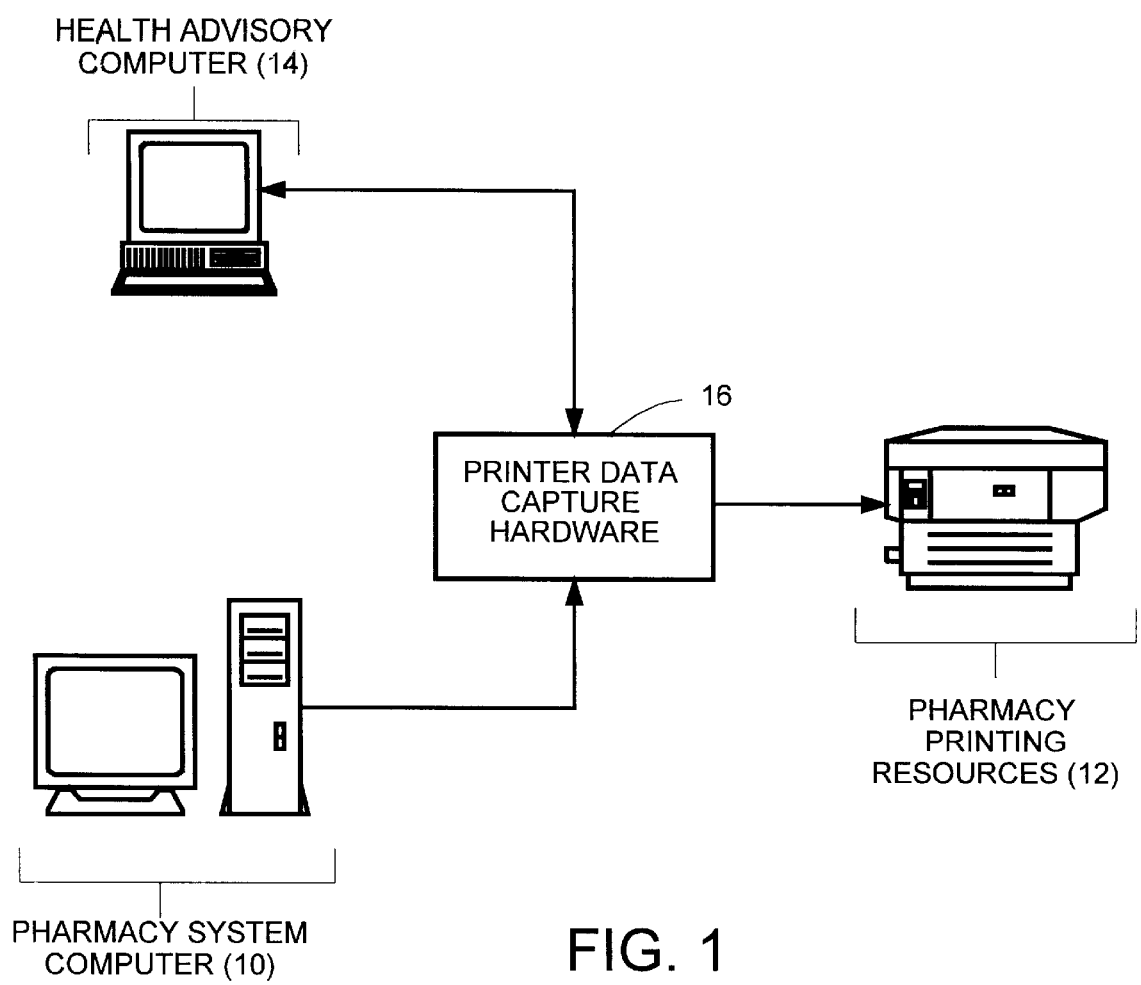
FIG. 1 is a top-level block diagram showing the hardware of the invention in relation to a pharmacy system computer and pharmacy printing resources.

As shown in the drawings for purposes of illustration, the present invention pertains to apparatus and a related method for automatically providing advisory information to pharmacy patients, based on the identification of the drugs being dispensed and on other information pertaining to the patient and to the prescription. Most approaches to supplying information to pharmacy patients require major modifications to the pharmacy computer system and do not appropriately target the advisory information, except to the extent that information may be provided based on the identification of the prescribed drug.

In accordance with the invention, an important aspect of which is illustrated in FIG. 1, data generated by a pharmacy system computer, indicated generally by reference numeral 10, and destined for a printer, indicated by the pharmacy printing resources 12, are captured in a passive manner for use in a health advisory computer 14, using printer data capture hardware 16. In some pharmacies, the printing resources 12 may include multiple printers for various reasons, to handle label and informational printing, or simply to handle a large volume of transactions. The hardware 16 may take a variety of forms, depending on the configuration of a specific pharmacy system to which the invention is to be adapted. Some pharmacy systems use two printers, one for printing labels and another, usually a laser printer, for printing advisory information for the patients. Other systems use only a single printer. Some systems use a serial printer interface, while others use a parallel interface. These different configurations result in different requirements for the printer data capture hardware 16, which will be discussed in more detail below. For the present, it is sufficient to note that the hardware 16 performs two principal functions. First, data destined for the pharmacy printing resources 12 are captured or tapped by the hardware 16 with only relatively simple changes in the pharmacy system computer 10. The changes needed include, for example, the addition of an "end-of-job" notification in a label print stream, to allow the health advisory computer 14 to determine when to start printing other advisory information, and changing the printable and non-printable information transmitted to the printer, to include such fields as age and gender. Basically, the health advisory computer 14 "eavesdrops" on output data being transmitted by the pharmacy system computer 10. Second, the hardware 16 may also provide an interface through which information generated in the health advisory computer 14 is transmitted to the printing resources 12. In general, the information is generated in the health advisory computer 14 based on selected components of the prescription and patient data captured in the hardware 16. The information is described in this specification as including "advisory messages," which is meant to be a broad term encompassing information pertaining to the dispensed product, promotional materials or coupons pertaining to prescription or non-prescription products, and news about pharmacy products or procedures, or pertaining to health in general.

Figure 2:
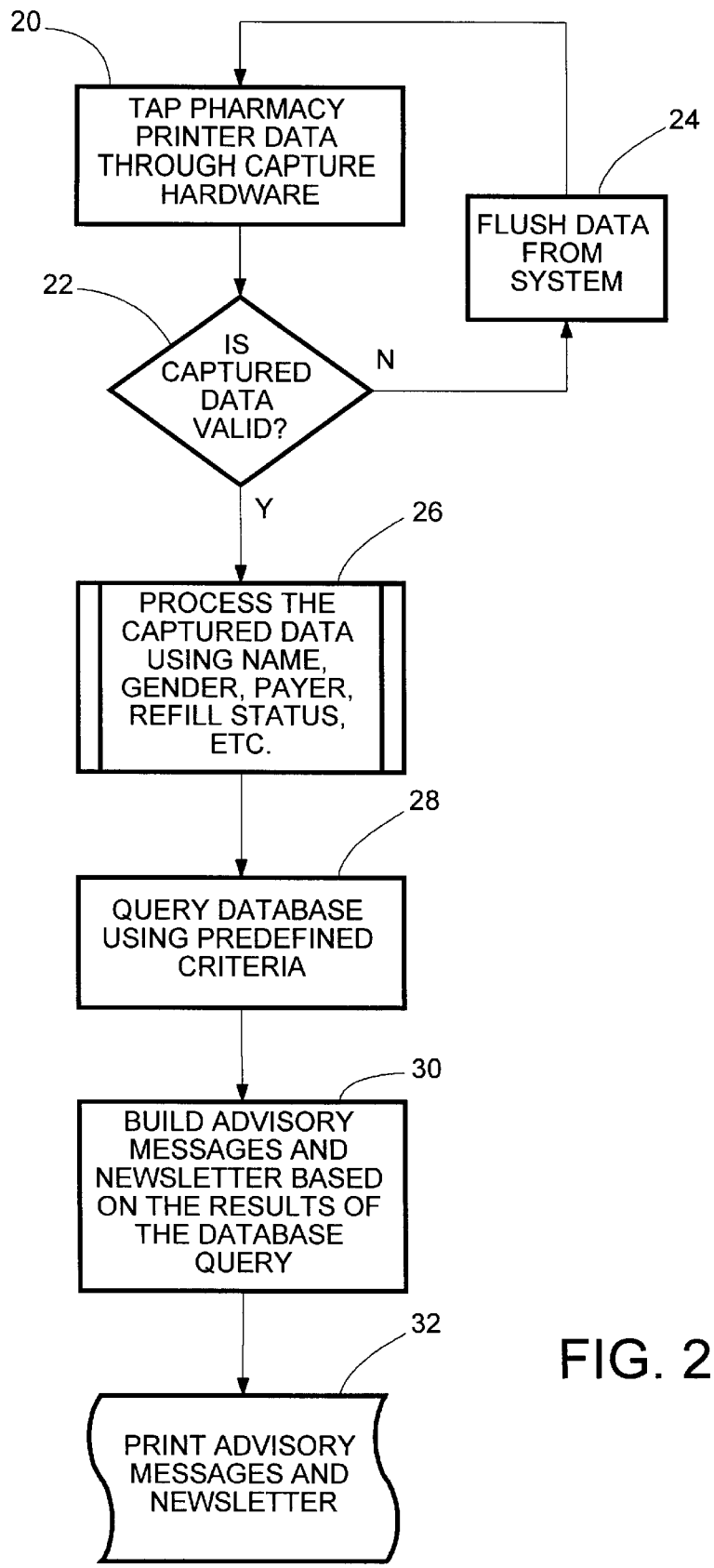
FIG. 2 is a flowchart of the functions performed in accordance with the method of the invention.

The functions performed in the health advisory computer 14 are depicted in the flowchart of FIG. 2. As shown in block 20, data destined for the pharmacy printing resources 12 are captured in the hardware 16 and sent to the computer 14 for processing. The computer 14 must be provided with knowledge of the transaction data format for a particular pharmacy system with which the invention is used. A validity check is performed, as indicated in block 22, to determine if the national drug code (NDC) and other data are valid for a particular transaction. If not, the captured data are flushed from the system, as indicated in block 24, and another set of data is captured. If the data set appears to be valid, the captured data are processed, as indicated in block 26, a database associated with the computer 14 is queried, as indicated in block 28, to determine which advisory messages, if any, should be delivered to the patient. The advisory messages, together with other standard items of message content, are compiled in an output buffer, as indicated in block 30, and finally printed as indicated in block 32. The printing step utilizes the printer data capture hardware 16 to provide for appropriate sharing of the printer resources 12 with the pharmacy system computer 10.

Targeting of information is based on the following factors associated with each transaction in which a prescription drug is dispensed:

The national drug code (NDC) uniquely identifying the drug.

The age of the patient.

The gender of the patient.

Whether the prescription is new or a refill.

The payer (insurance company, if any).

Age specific targeting is useful in a variety of contexts. An example is the dispensing of oral contraceptives, which are sometimes prescribed to young women not for birth control but to promote regularity of the menstrual cycle. One type of advisory message, concerning birth control and recommendations for preventing sexually transmitted diseases, might not be thought suitable for female children under twelve years of age. In accordance with this aspect of the invention, the message can be tailored by age.

Gender specific targeting also is useful, because some drugs are used by both men and women, but for different purposes. For example, the drug Metronodazol is commonly prescribed for women, to treat non-specific vaginal infections, but is also prescribed to control pimples and more serious infections, such as tetanus, in both men and women. The advisory message can be tailored appropriately depending whether the patient is a man or a woman.

If the patient's "payer," whether private insurance company, the patient, Medicare or Medicaid, is known, advisory information can be appropriately targeted to the patient. For example, different insurers have a different "disease state protocols," which are recommended procedures for treatment of patients having various diseases. A patient with Type II diabetes, for example, may be required by an insurance company to have a bi-annual blood panel to help physicians monitor the progress of the disease and its treatment adequately. Appropriate advisory messages can, therefore, be generated based on the identity of the insurer, if any. Even self-insuring patients can be advised of the desirability of follow-up diagnostic tests for the condition being treated.

Whether the prescription is new or a refill is also information that can be used to generate different types of advisory messages. The refill patient may not need all the information provided to the new patient, or the refill patient may need to be reminded about an insurer's policies regarding refills.

The age ranges employed in the system of the invention are a matter of design choice, but narrower ranges are needed for growing children than for mature adults. In the presently preferred embodiment of the invention, the following age ranges are used: 0–1, 2–4, 5–11, 12–18, 19–25, 26–35, 36–45, 46–60, and over 60.

Each different combination of factors (NDC, age, gender, new/refill, and payer) may be used to trigger generation of a different advisory message. The various combinations selected to trigger a message are stored in a database or trigger matrix associated with the health advisory computer 14, and this trigger matrix is queried, as indicated in block 28 of the FIG. 3 flowchart, to determine which, if any, advisory messages are to be printed.

Figure 3:
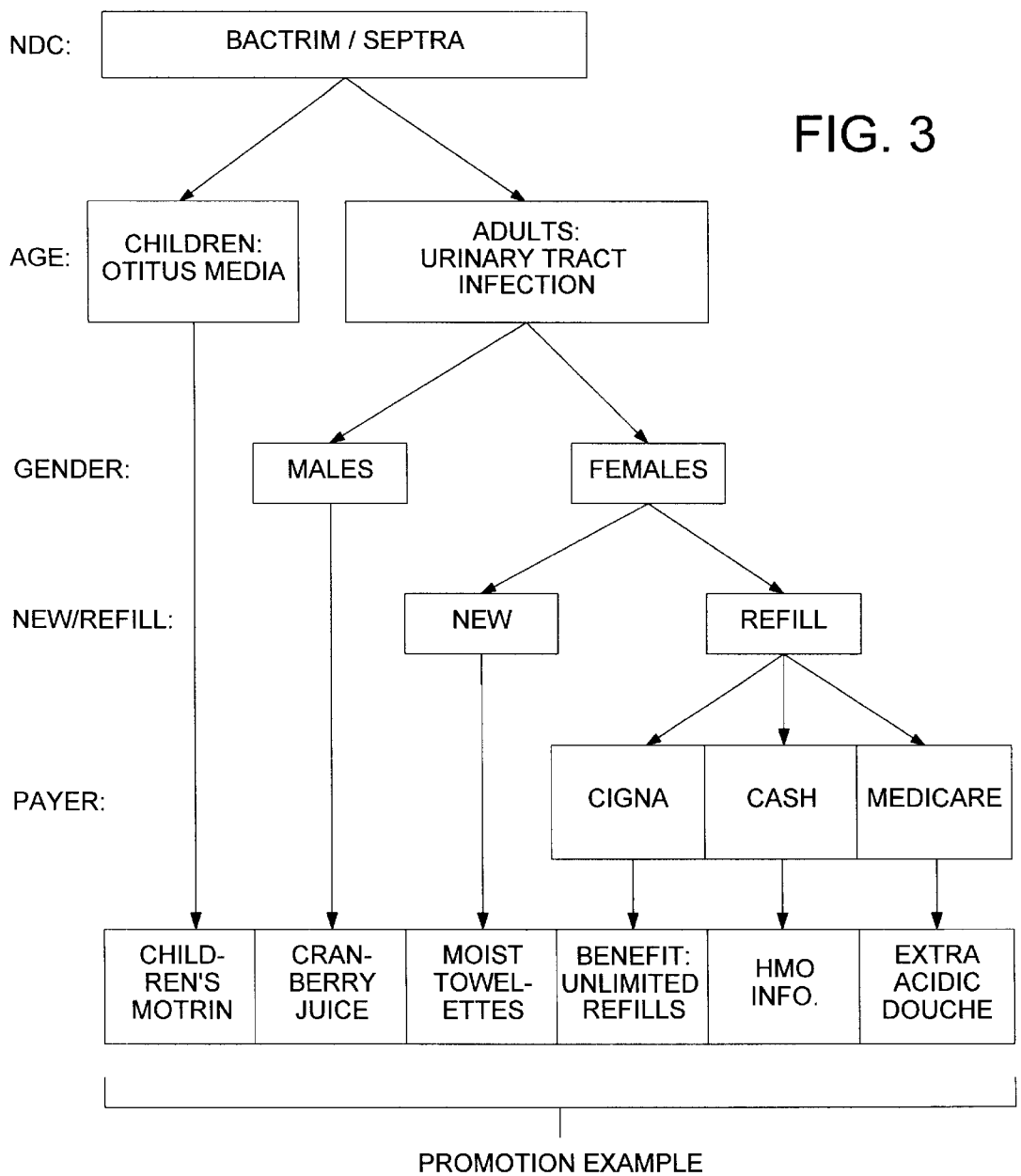
FIG. 3 is a block diagram depicting an example of a promotion using the principles of the invention.

An example of printing a promotional message in response to a combination of data factors is given in FIG. 3. The drugs Bactrim and Septra (brands of Sulfamethoxazole-Trimethoprim) are used differently based on age of the patient. For children, the drugs may be used to treat middle ear infections (otitis media) and an appropriate advisory message might point out the desirability of taking children's Motrin (an anti-inflammatory drug), but for adults the same drug is used to treat urinary tract infections. Within the adult category, men and women would typically need different advisory information. For a man, the advisory message may point out the advisability of drinking cranberry juice. For a woman, different treatment may be advisable. Further, as shown in the figure, new and refill prescriptions may be treated differently, and the advisory message may also be affected by the identity of the payer.

Figure 4:
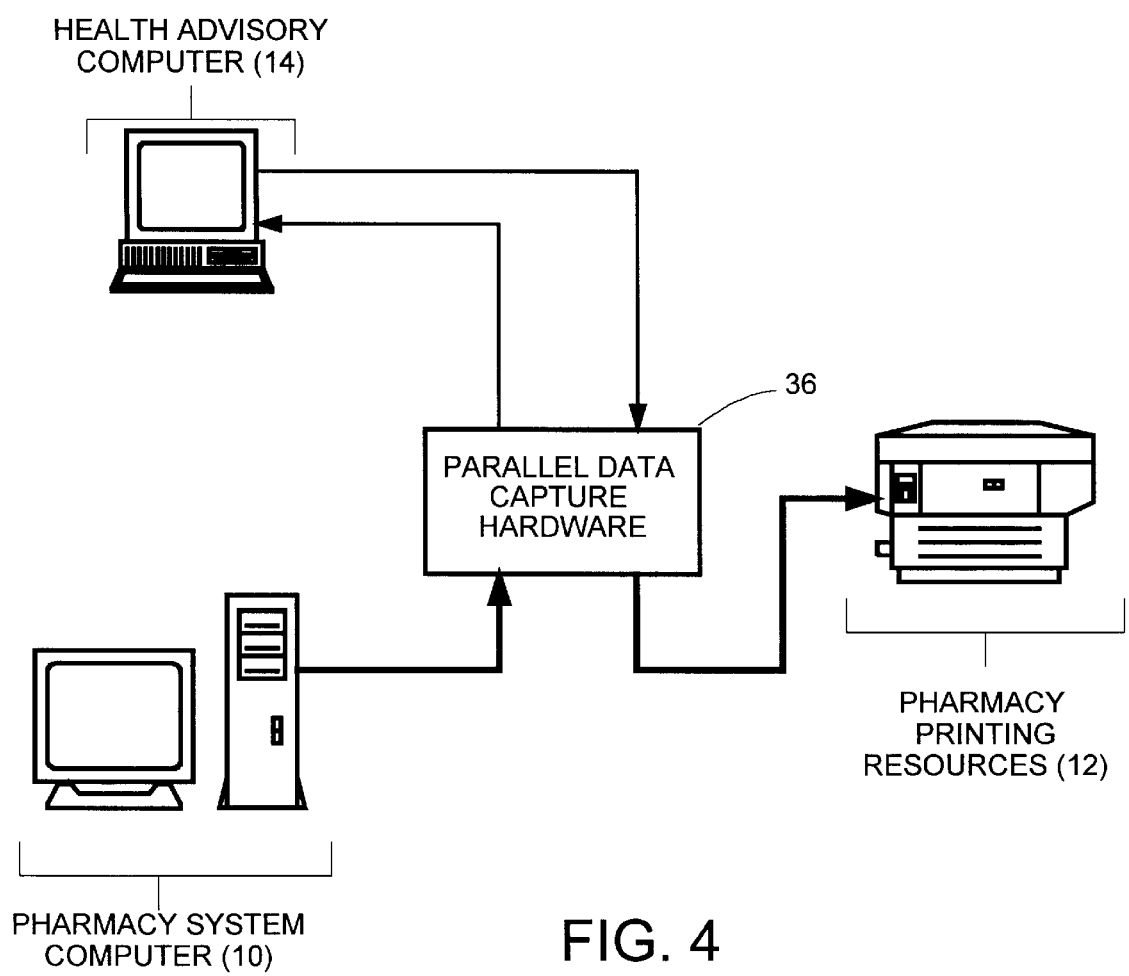
FIG. 4 is a block diagram similar to FIG. 1 and showing one configuration of printer data capture hardware.

Some of the different configurations of the printer data capture hardware 16 (FIG. 1) will now be discussed in more detail. FIG. 4 shows a preferred embodiment using a parallel printer and parallel data capture hardware 36. In this configuration, the pharmacy system computer 10 normally outputs in parallel format to a parallel printer, but in accordance with the invention the parallel printer cable is diverted through the parallel data capture hardware 36.

The term "parallel" refers to a commonly used mode of transmission of data from a computer system to a peripheral device, such as a printer or another computer, wherein binary data is formatted into "bytes" of eight or more data bits for transmission over parallel conductors in a cable. For "serial" data transmission, the data bits are transmitted bit-by-bit over a single pair of conductors in a serial data cable.

Parallel data arriving from the pharmacy system computer 10 are converted to a serial format in the hardware 36, and transmitted in serial form to the health advisory computer 14. The parallel data stream entering the hardware 36 also continues through the hardware box 36 and is transmitted to the printing resources 12, which in this case consist of a single parallel printer. The health advisory computer 14 processes the serial data in accordance with the functions described above with reference to FIGS. 2 and 3, and generates advisory messages in the form of a parallel output stream directed back to the parallel data capture hardware 36. The latter also has the function of mediating any conflict for the printer between data arriving from the health advisory computer 14 and data arriving from the pharmacy system computer 10. This mediation is best implemented as a first-come-first-served protocol with appropriate timers to determine when an printer output has ended. For example, when data stops coming from the pharmacy system computer 10 for 2–3 seconds, the output can be considered completed. The hardware 36 then waits for printer data from the health advisory computer 14. If no such data are received within, say, two seconds, it can be assumed that no advisory messages will be printed and the hardware 36 returns to a default mode in which it waits for more data from the pharmacy system computer 10. If the health advisory computer 14 sends print data and then ceases transmission, its output will be considered complete after a pause of more than two seconds, and the hardware 36 also returns to the default mode. Basically, an operation cycle will always begin with the pharmacy system computer 10 initiating printing of a product label. At the same time, the captured transaction data are analyzed by the health advisory computer 14, which may then print an associated advisory message.

Figure 5:
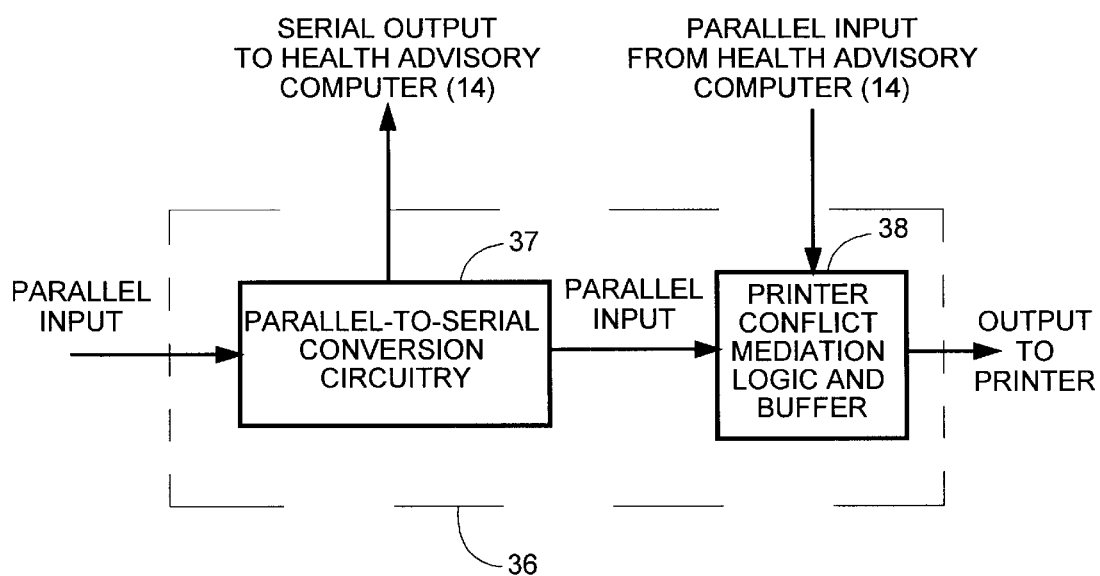
FIG. 5 is a simplified block diagram of the parallel data capture hardware shown in FIG. 4.

FIG. 5 shows the principal components of the hardware 36 of FIG. 4. Parallel input data from the pharmacy system computer 10 are converted to serial data in parallel-to-serial conversion circuitry 37. The corresponding data stream in serial form is output to the health advisory computer 14 and the parallel input data stream continues through the hardware 36. A parallel data stream output from the health advisory computer 14 is merged with the parallel stream from the pharmacy system computer 10, in printer conflict mediation logic 38, which includes a storage buffer for the temporary storage of data when the printer is busy.

Figure 6:
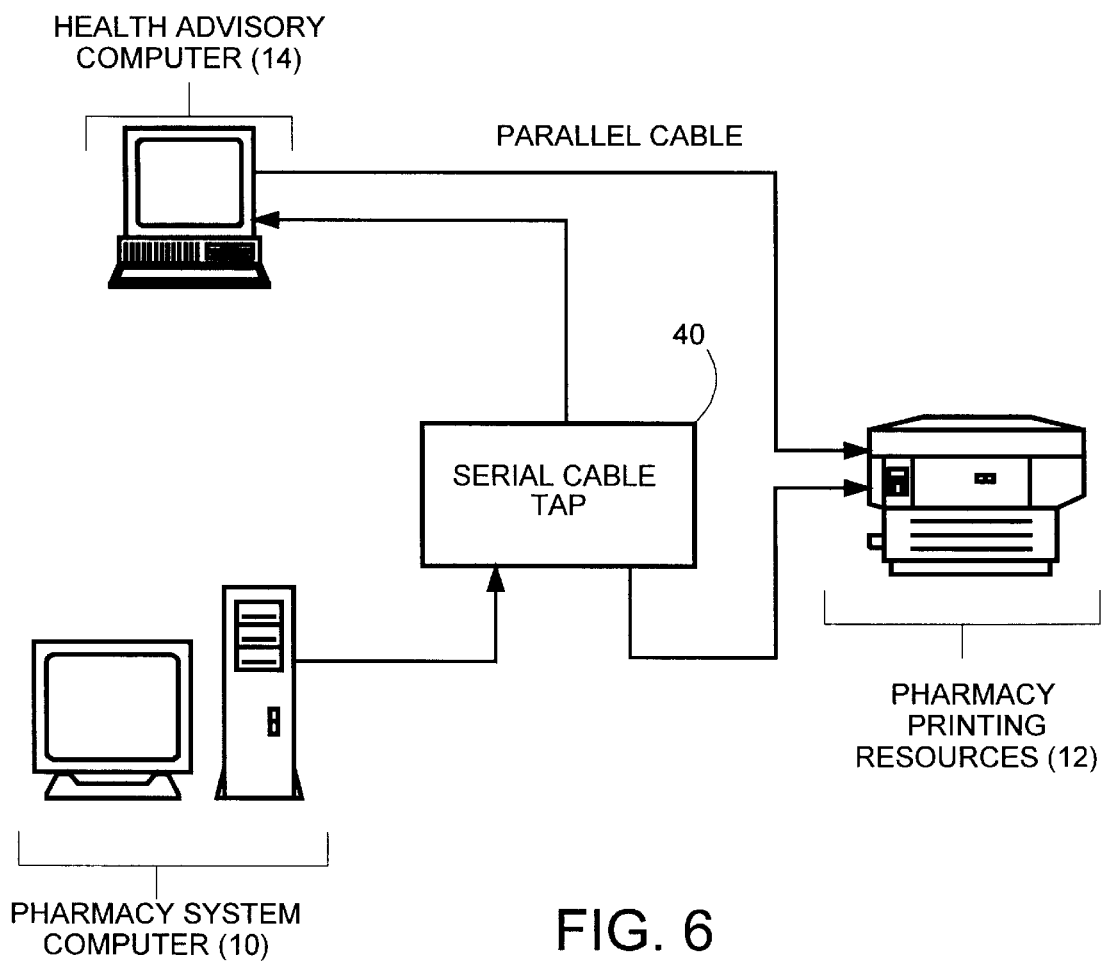
FIG. 6 is a block diagram similar to FIG. 4, but showing an alternative configuration of printer data capture hardware.

FIG. 6 is a slightly different configuration, in which an existing pharmacy system computer 10 outputs data in serial form. In this case, the data capture hardware can take the form of a serial cable tap 40, which simply splits the serial data into two paths, one of which continues to a serial port of the printer 12, and the other of which is diverted to the health advisory computer 14. Advisory messages are output over a parallel cable to the same printer 12, which has both a serial port and a parallel port, and further includes logic to mediate any conflicts that arise between the two inputs. Many conventional laser printers have this capability.

Figure 7:
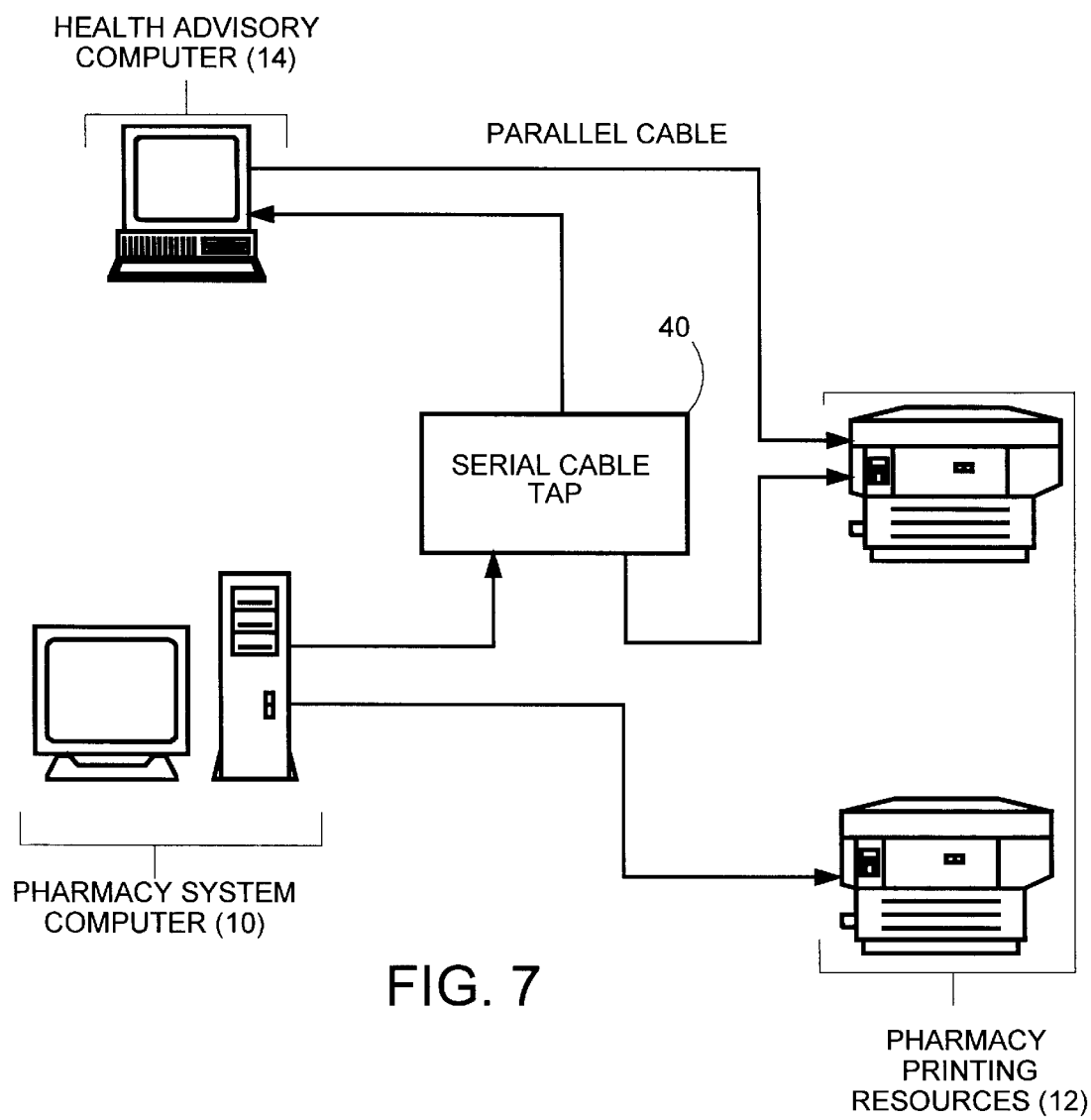
FIG. 7 is a block diagram similar to FIG. 6, but showing an additional pharmacy label printer in the configuration.

FIG. 7 is yet another configuration, in which the existing pharmacy system computer 10 has two serial output ports, one directed to a label printer and the other directed to an auxiliary printer for advisory messages. The serial cable tap 40 is again used to eavesdrop on data sent to the auxiliary printer, and to generate appropriate additional advisory messages for transmission to the printer over a parallel cable, in the same was as described with reference to FIG. 6.

It will be appreciated that various other hardware configurations may be used to eavesdrop or tap into printer data being generated by the pharmacy system computer, and the invention is not limited to the specific configurations described here by way of example. Whether serial or parallel data ports and cables are used is dictated primarily by the configuration of the existing pharmacy system. Moreover, the types of cable connectors used are not critical to the invention.

The invention represents a significant advance in the field of point-of-sale systems in the pharmacy environment. More specifically, the invention provides for targeting of information to pharmacy patients, taking into account important factors such as age, gender, prescription status, and payer identity, as well as the identification of the drug being dispensed. Further, the invention achieves these goals without major modification of existing pharmacy computer systems. An added advantage is that, because the apparatus of the invention taps passively into the pharmacy system print stream, any malfunction of the invention has no affect on the basic operation of the pharmacy system, which can continue to process prescriptions and print labels.

The ability of the invention to provide targeted information to patients can be extended to the provision of product samples that are similarly targeted, based on the same patient factors determined from the print data stream of the pharmacy system. Yet another advantage of the invention is that, if the health advisory computer 14 is connected to a network of similar computers, advisory messages can be directed to pharmacists over this network and printed on the pharmacy printer.

It will be appreciated that, although a number of specific embodiments of the invention have been described in detail for purposes of illustration, various modifications may be made without departing from the spirit and scope of the invention. Accordingly, the invention should not be limited except as by the appended claims.

We claim:

1. A method for generating targeted messages to pharmacy patients, said method comprising the steps of:
    capturing a data record transmitted to a pharmacy printer from a pharmacy computer, said data record including components pertaining to a pharmacy transaction in which a pharmacy product is dispensed to a patient;
    comparing selected components of said captured data record with components in a database to determine contents of an advisory message;
    building said advisory message based on determinations made in said comparing step; and
    transmitting said advisory message to said pharmacy printer, so as to print said advisory message based on said selected components of said captured data record.

2. The method of claim 1, wherein said comparing step comprises comparing selected components of said captured data record including an age of said patient and an identity of said pharmacy product.

3. The method of claim 1, wherein said comparing step comprises comparing selected components of said captured data record including a gender of said patient and an identity of said pharmacy product.

4. The method of claim 1, wherein said comparing step comprises comparing selected components of said captured data record including an identity of an entity primarily responsible for payment to said pharmacy for said pharmacy transaction and an identity of said pharmacy product.

5. The method of claim 1, wherein said comparing step comprises comparing selected components of said captured data record including an indication of whether said pharmacy transaction includes a new or a refill prescription for said pharmacy product, and an identity of said pharmacy product.

6. The method of claim 1, wherein said comparing step comprises comparing selected components of said captured data record including an identity of said pharmacy product and at least one of an age of said patient, a gender of said patient, an identity of an entity primarily responsible for payment to said pharmacy for said pharmacy transaction, and whether said pharmacy transaction includes a new or a refill prescription for said pharmacy product.

7. The method as defined in claim 1, further including the step of distributing to said patient a product sample to accompany said advisory message.

8. An apparatus for generating targeted messages to pharmacy patients, for use in a pharmacy computer system having a pharmacy processor and at least one printer, the apparatus comprising:
    a hardware interface coupled between said pharmacy processor and said at least one printer, for capturing a data record transmitted to said at least one printer from said pharmacy computer system, said data record including components pertaining to a pharmacy transaction in which a pharmacy product is dispensed to a patient;
    a database containing components used for building an advisory message; and
    an additional processor coupled to said database and said hardware interface, for comparing selected components of said captured data record with said components in said database to determine contents of said advisory message, and for building said advisory message;
    wherein one of said hardware interface and said additional processor includes means for transmitting said advisory message to said at least one printer, whereby said advisory message is printed on said at least one printer based on said selected components of said captured data record.

9. The apparatus of claim 8, wherein said selected components of said captured data record include an age of said patient and an identity of said pharmacy product.

10. The apparatus of claim 8, wherein said selected components of said captured data record include a gender of said patient and an identity of said pharmacy product.

11. The apparatus of claim 8, wherein said selected components of said captured data record include an identity of an entity primarily responsible for payment to said pharmacy for said pharmacy transaction and an identity of said pharmacy product.

12. The apparatus of claim 8, wherein said selected components of said captured data record include an indication of whether said pharmacy transaction includes a new or a refill prescription for said pharmacy product, and an identity of said pharmacy product.

13. The apparatus of claim 8, wherein said selected components of said captured data record include an identity of said pharmacy product and at least one of an age of said patient, a gender of said patient, an identity of an entity primarily responsible for payment to said pharmacy for said pharmacy transaction, and whether said pharmacy transaction includes a new or a refill prescription for said pharmacy product.

14. The apparatus of claim 8, wherein said pharmacy computer system transmits said data record in parallel format to said at least one printer;
    said hardware interface includes a parallel-to-serial data converter coupled to said means for transmitting, for capturing said data record transmitted in parallel format, and for transmitting said data record in serial format to said additional processor; and said means for transmitting transmits said advisory message to said at least one printer and includes a parallel data connection to said additional processor for receiving said advisory message in parallel format, and further includes means for mediating printer conflicts arising between data records transmitted from said pharmacy computer system and advisory messages received from said additional processor.

15. The apparatus of claim 8, wherein said pharmacy computer system transmits said data record in serial format to said at last one printer;

said hardware interface includes a serial tap for capturing said data record transmitted in serial format, and for transmitting said data record in serial format to said additional processor and said at least one printer;

said additional processor transmits said advisory message in parallel format to said at least one printer; and said least one printer further includes means for mediating printer conflicts arising between data records transmitted from said serial tap of said hardware interface and advisory messages received from said additional processor.

16. The apparatus of claim 8, wherein said at least one printer comprises a first printer for printing said advisory message and a second printer for printing a label for said pharmacy product;

said pharmacy computer system transmits said data record in serial format to said first and second printers;

said hardware interface includes a serial tap for capturing said data record transmitted in serial format to said first printer, and for transmitting said data record in serial format to said additional processor and said first printer;

said additional processor transmits said advisory message in parallel format to said first printer; and said first printer further includes means for mediating printer conflicts arising between data records transmitted from said serial tap of said hardware interface and advisory messages received from said additional processor.

* * * * *